United States Patent [19]

Yamazaki et al.

[11] 4,186,266

[45] Jan. 29, 1980

[54] PROCESS FOR PRODUCING 5-FLUOROURACIL

[75] Inventors: Akihiro Yamazaki, Yokosuka; Hirokazu Morisawa, Kawasaki; Yoshio Oda, Yokohama; Keiichi Uchida, Kawasaki, all of Japan

[73] Assignees: Asahi Glass Company Limited; Ajinomoto Company Incorporated, both of Tokyo, Japan

[21] Appl. No.: 913,333

[22] Filed: Jun. 7, 1978

[30] Foreign Application Priority Data

Jun. 17, 1977 [JP] Japan .................................. 52-70981

[51] Int. Cl.² .......................................... C07D 239/54

[52] U.S. Cl. .................................................. 544/313
[58] Field of Search ........................................ 544/313

[56] References Cited

U.S. PATENT DOCUMENTS 2,802,005  8/1957  Heidelberger et al. ............. 544/313
3,954,758  5/1976  Schuman et al. ..................... 544/313

*Primary Examiner*—Paul M. Coughlan, Jr.
*Attorney, Agent, or Firm*—Oblon, Fisher, Spivak, McClelland & Maier

[57] ABSTRACT

5-Fluorouraacil is produced by reacting orotic acid with a fluorinating agent and then, decarboxylating the resulting 5-fluoro-orotic acid.

11 Claims, No Drawings

PROCESS FOR PRODUCING 5-FLUOROURACIL

BACKGROUND OF THE INVENTION

The present invention relates to a process for producing 5-fluorouracil. More particularly, it relates to a novel process for producing 5-fluorouracil from a starting material of orotic acid in advantageous manners by a combination of a fluorination and a decarboxylation.

It has been known that 5-fluorouracil is useful as an antitumour agent or in an intermediate for various antitumour agents.

Various syntheses of 5-fluorouracil have been proposed. For example, the synthesis of 5-fluorouracil by using ethylmonofluoroacetate as a starting material has been disclosed in U.S. Pat. No. 2,802,005 and Japanese Patent Publication No. 9578/1961. This process has disadvantages of the use of the toxic starting material and many steps and low yield of the object product, in an industrial production.

It has been also proposed to produce 5-fluorouracil by a fluorination of uracil with a fluorinating agent such as fluorine gas and trifluoromethyl hypofluorite in Japanese Patent Publication No. 25476/1975, U.S. Pat. No. 3,682,917, Japanese Unexamined Patent Publication Nos. 9127/1972 and 149,287/1976.

In accordance with the studies, the following disadvantages have been found in the process for producing 5-fluorouracil by a fluorination of uracil with a fluorinating agent.

The solubility of uracil to water is similar to that of 5-fluorouracil whereby it is not easy to isolate the unreacted uracil by a recrystallization, etc. Accordingly, in the conventional process, the fluorination should be completed to control the residue of the unreacted uracil. However, the fluorination is a severe exothermic reaction whereby a decomposition or a modification of the object product may be caused if the complete fluorination is performed. That is, high conversion leads to low selectivity to the object product. If the conversion is lowered for high selectivity, the trouble of recovery and recycle of the unreacted uracil is caused because of said difficulty of the isolation of the object product.

SUMMARY OF THE INVENTION

It is an object of the present invention to provide a novel process for producing 5-fluorouracil in high yield from a starting material orotic acid in advantageous manners by a combination of a fluorination and a decarboxylation without said disadvantages.

The foregoing and other objects of the present invention have been attained by reacting orotic acid with a fluorinating agent and then, decarboxylating the resulting 5-fluoro-orotic acid.

DETAILED DESCRIPTION OF THE PREFERRED EMBODIMENTS

In the process of the present invention, orotic acid is easily converted to 5-fluoro-orotic acid by the fluorination with a fluorinating agent and the resulting 5-fluoro-orotic acid is converted to 5-fluorouracil by the decarboxylation.

The solubility of orotic acid to water is remarkably low in comparison with those of 5-fluorouracil and 5-fluoro-orotic acid whereby orotic acid can be easily isolated from 5-fluorouracil and 5-fluoro-orotic acid. A decarboxylation of orotic acid is not easily performed, however, the decarboxylation of 5-fluoro-orotic acid is relatively easy to produce 5-fluorouracil.

As stated above, orotic acid is easily isolated from 5-fluoro-orotic acid in the fluorination step and it is also easily isolated from 5-fluorouracil in the decarboxylation step depending upon the difference of solubilities thereof whereby the object product of 5-fluorouracil which does not contain the unreacted orotic acid can be smoothly and advantageously obtained.

The unreacted orotic acid can be easily isolated, recovered and recycled whereby it is unnecessary to attain high conversion in the fluorination step.

Thus, the process of the present invention has been accomplished depending upon the above-mentioned considerations, to provide the novel process for producing 5-fluorouracil which comprises reacting orotic acid with a fluorinating agent and then, decarboxylating the resulting 5-fluoro-orotic acid.

In accordance with the process of the present invention, 5-fluorouracil having high purity can be smoothly and advantageously obtained in high yield in an industrial process.

The process of the present invention is the combination of the fluorination step and the decarboxylation step and high yield of the object product as that of the fluorination or uracil can be attained. Moreover, the isolation and recovery of the unreacted orotic acid is easily attained whereby the process of the present invention is significantly superior to the conventional processes.

The starting material of orotic acid is easily available at low cost so as to be significantly advantageous in an industrial operation.

The starting material of orotic acid used in the process of the present invention can be obtained in various forms and preferably in a form of monohydrate from the viewpoint of easy availability and others.

Firstly, orotic acid is reacted with a fluorinating agent.

The typical fluorinating agent is fluorine gas and it can be also trifluoromethyl hypofluorite ($CF_3OF$) and xenon fluoride ($XeF_2$), etc.

When fluorine gas is used, it is preferable to dilute fluorine gas with an inert gas in order to prevent the vigorous reaction.

Nitrogen is usually used as the inert gas from the viewpoint of easy availability. The inert gas can be also argon, helium, carbon dioxide gas and sulfur hexafluoride. For example, suitable result is attained by using fluorine gas diluted with 0.5 to 50 vol. times preferably 1 to 10 vol. times of an inert gas to fluorine gas.

The reaction of orotic acid with the fluorinating agent is preferably carried out in an inert liquid medium which is substantially inert to the fluorinating agent. That is, it is preferable to use a liquid medium which is substantially inert to the fluorinating agent in the condition of the fluorination of the present invention.

Suitable liquid media include trifluoroacetic acid, water, hydrofluoric acid, sulfuric acid, formic acid, acetic acid, perfluoroalkanols and mixtures thereof. It is preferable to use a polar solvent.

The polar solvents containing water such as aqueous solution of formic acid are especially suitable as the liquid medium.

In order to perform the smooth reaction, it is preferable to uniformly disperse orotic acid in the liquid medium. It is preferable to react the fluorinating agent in a form of a solution or a dispersion.

The operation and condition of the fluorination of orotic acid with the fluorinating agent are preferably selected depending upon the kinds of the fluorinating agent and other factors. When fluorine gas is used, it is preferable to dilute it with the inert gas as described, and it is preferable to react to about −50° C. to +100° C. especially about −10° C. to +70° C. under controlling the feeding rate of the fluorine containing gas depending upon the kind of the liquid medium etc. and it is preferable to feed the fluorine gas diluted with about 1 to 10 vol. times of the inert gas at a ratio of about 20 to 5000 ml/min. per 1 mole of the starting material of orotic acid.

In usual, the fluorine gas is fed at a ratio of less than 3 mole preferably 1.2 to 2.0 mole of the fluorine gas per 1 mole of orotic acid.

It is also possible to perform the fluorination at low temperature of about −80° C. to +30° C. by using hypofluorinate as the fluorinating agent.

According to infrared spectrum and NMR spectrum analysis, it is found that the intermediate (adduct) having the formula

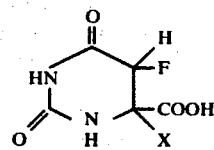

wherein X represents OH, $CF_3COO$, $CH_3COO$, HCOO, F and other nucleophilic group derived from the solvent may be formed by reacting orotic acid with fluorine gas in the liquid medium in the fluorination step of the present invention.

The intermediate adducts are easily soluble in water, alcohols and other solvents. Accordingly, the unreacted orotic acid can be easily isolated by dissolving the intermediate adduct in water by adding water to the solid reaction mixture obtained by removing the solvent after the fluorination.

The intermediate adducts are relatively stable at room temperature and are easily converted into 5-fluoro-orotic acid as the following equation by heating it in suitable solvent such as water at higher than 60° C. or heating the solid reaction mixture in air at about 100° to 160° C.

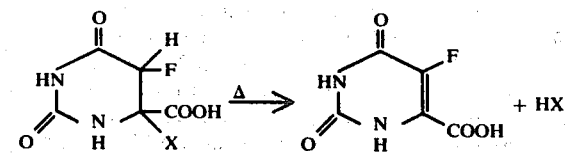

Sometimes, 5-fluoro-orotic acid can be directly obtained without detecting the intermediate adduct depending upon the condition of the fluorination.

These descriptions should not be considered to limit the scope of the present invention and should be considered to easily understand the present invention.

In the fluorination, 5-fluoro-orotic acid is produced by reacting orotic acid with the fluorinating agent.

The resulting 5-fluoro-orotic acid can be easily recrystallized from a solvent such as water and alcohols by the conventional process.

The resulting 5-fluoro-orotic acid can be easily converted into 5-fluorouracil by the decarboxylation which can be performed by heating it at about 130° to 290° C. preferably about 140° to 260° C.

In the step, it is possible to perform the dehydration and the decarboxylation by heating 5-fluoro-orotic acid monohydrate.

In order to easily perform the decarboxylation, it is possible to use 5-fluoro-orotic acid after converting it to a desirable derivative thereof. It is also possible to perform the decarboxylation by suitable other manners.

The simple decarboxylation is carried out by charging 5-fluoro-orotic acid in a reactor and then, dipping the reactor in a thermal medium heated at about 250° C.

The decarboxylation can be performed in air, or an inert gas such as nitrogen gas in vacuum or under a reduced pressure. It is preferable to perform the decarboxylation in an atmosphere which does not contain oxygen.

The decarboxylation can be also performed by suspending 5-fluoro-orotic acid in suitable high boiling point medium and heating them beside the above-mentioned manner of direct heating of the solid 5-fluoro-orotic acid.

In the process of the present invention, it is also possible to perform both of the conversion of the intermediate adduct into 5-fluoro-orotic acid by the heating and the decarboxylation of 5-fluoro-orotic acid.

For example, 5-fluorouracil can be obtained by heating the intermediate adduct obtained by the fluorination of orotic acid in water. In the heating of the intermediate adduct in water, carbon dioxide gas is formed by the decarboxylation to raise the pressure in the reaction system. The intermediate adduct has significantly higher solubility to water in comparison with that of the starting material of orotic acid whereby the isolation of them is significantly easy.

The crude 5-fluorouracil obtained by the decarboxylation step can be purified to obtain the pure product by recrystallizing from a solvent such as water and alcohols.

The purity of the product can be further increased by suitable purification such as treatment with an activated carbon or an ion-exchange resin.

The invention will be further illustrated by certain examples.

EXAMPLE 1

In a 300 ml reactor made of polytetrafluoroethylene, 25 g of orotic acid monohydrate ($C_5H_4N_2O_4 \cdot H_2O$) and 200 ml of trifluoroacetic acid (solvent) were charged and a mixed gas of fluorine gas (40 ml/min.) and nitrogen gas (80 ml/min.) was fed into the mixture under stirring to react them at 0° to 10° C. for 3 hours. After the reaction, the reaction mixture was analyzed by the NMR analysis and the IR analysis whereby no unreacted orotic acid monohydrate was found.

The solvent was distilled off from the reaction mixture and the residue was dissolved in 300 ml of water and the solution was boiled for 1.5 hours and concentrated and then, the concentrate was kept at 0° C. to obtain 22.1 g of crystals of 5-fluoro-orotic acid monohydrate (yield: 80% based on orotic acid).

The crystals were heated at 240° C. to perform the dehydration and the decarboxylation and the resulting product was recrystallized from water to obtain 11.9 g of 5-fluorouracil ($C_4H_3N_2O_2F$) (yield: 64% based on orotic acid). The purity of the resulting 5-fluorouracil was higher than 99.9%.

EXAMPLE 2

In a 300 ml reactor made of polytetrafluoroethylene, 18 m mole of trifluoromethyl hypofluorite ($CF_3OF$) in 150 ml of trichloromonofluoromethane ($CFCl_3$) were charged and the reactor was cooled at $-78°$ C. in dry-ice-ethanol bath.

A suspension of 2 g of orotic acid monohydrate in a mixed solvent of 20 ml of trifluoroacetic acid and 20 ml of water was added to the mixture in the reactor under vigorously stirring with a magnetic stirrer and the temperature of the mixture was gradually elevated from $-78°$ C. to room temperature and the reaction was continued for about 20 hours.

The unreacted trifluoromethyl hypofluorite was removed by bubbling nitrogen gas and the residual solvent was removed under a reduced pressure. The resulting residue was dissolved in 100 ml of water and the solution was boiled for about 3 hours and then, concentrated and the concentrate was kept at $0°$ C. to obtain 1.9 g of crystals of 5-fluoro-orotic acid monohydrate (yield: 86%). The crystals were heated at $240°$ C. to perform the decarboxylation and 1.2 g of 5-fluorouracil was obtained.

EXAMPLE 3

In the example, 20 g of crystals of 5-fluoro-orotic acid monohydrate obtained by the fluorination and the post-treatment of Example 1 was suspended in 80 ml of triethyleneglycol dimethyl ether and the mixture was heated under stirring whereby water was generated at higher than $130°$ C. and carbon dioxide was generated at higher than $190°$ C. The decarboxylation was completed by heating at $200°$ C. for about 20 minutes. After cooling the reaction mixture, the reaction product was separated by a filtration and recrystallized from water to obtain 12.2 g of 5-fluorouracil. The yield was 90% based on 5-fluoro-orotic acid monohydrate.

EXAMPLE 4

In a 1 liter reactor made of stainless steel SUS-316L, 40 g of orotic acid monohydrate ($C_5H_4N_2O_4.H_2O$) and 350 ml of aqueous solution of formic acid (88 wt. %) were charged and a mixed gas of fluorine gas (28 ml/min.) and nitrogen gas (112 ml/min) was fed into the mixture under stirring to react them at $8°$ to $15°$ C. for 5.5 hours. After the reaction, the solvent was recovered under a reduced pressure at $65°$ C. and the residue was dissolved in 200 ml of water and the solution was filtered and the filtrate was boiled for 1 hour and then, concentrated and the concentrate was kept at $0°$ C. to obtain 37.5 g of pale yellow crystals which was confirmed to be 5-fluoro-orotic acid monohydrate by the IR analysis and the NMR an analysis.

In the reaction, the conversion of the orotic acid monohydrate was 100% and the yield of 5-fluoro-orotic acid monohydrate was 85.0%. The crystals were heated at $260°$ C. under a reduced pressure of lower than 1 mmHg to perform the decarboxylation to obtain 22.5 g of 5-fluorouracil.

What is claimed is:

1. A process for producing 5-fluorouracil in high yield and of high purity from orotic acid, which comprises reacting orotic acid with a fluorinating agent to form 5-fluoro-orotic acid, separating any unreacted orotic acid, and then heating the 5-fluoro-orotic acid to decarboxylate it and obtain 5-fluorouracil.

2. The process according to claim 1, wherein the product of decarboxylation is recrystallized from water to obtain 5-fluorouracil.

3. The process according to claim 1 wherein the fluorinating agent is trifluoromethyl hypofluorite.

4. The process according to claim 1 wherein said fluorinating agent is diluted with an inert gas.

5. The process according to claim 1 wherein the reaction of orotic acid with a fluorinating agent is conducted in a liquid medium which is substantially inert to the fluorinating agnet.

6. The process according to claim 1 wherein the reaction of orotic acid with a fluorinating agent is conducted at $-50°$ C. to $+100°$ C.

7. The process according to claim 1 wherein the reaction is conducted by feeding fluorine gas at a feed rate of 20 to 5000 ml/min per 1 mole of orotic acid.

8. The process according to claim 1 wherein the orotic acid is orotic acid monohydrate.

9. The process according to claim 1, wherein said decarboxylation is conducted by heating 5-fluoro-orotic acid.

10. The process according to claim 9, wherein the temperature of decarboxylation is in a range of $130°$ to $290°$ C.

11. The process according to claim 1, wherein said fluorinating agent is fluorine gas.

* * * * *